United States Patent
Marshall et al.

(10) Patent No.: US 10,842,916 B2
(45) Date of Patent: Nov. 24, 2020

(54) INJECTABLE POROUS DEVICE FOR TREATMENT OF DRY AND WET AGE-RELATED MACULAR DEGENERATION OR DIABETIC RETINOPATHY

(71) Applicant: HEALIONICS CORPORATION, Seattle, WA (US)

(72) Inventors: Andrew J. Marshall, Seattle, WA (US); Max Maginness, Seattle, WA (US)

(73) Assignee: HEALIONICS CORPORATION, Seattle, WA (US)

( * ) Notice: Subject to any disclaimer, the term of this patent is extended or adjusted under 35 U.S.C. 154(b) by 0 days.

(21) Appl. No.: 15/192,867

(22) Filed: Jun. 24, 2016

(65) Prior Publication Data
US 2016/0375178 A1 Dec. 29, 2016

Related U.S. Application Data

(60) Provisional application No. 62/204,877, filed on Aug. 13, 2015, provisional application No. 62/184,151, filed on Jun. 24, 2015.

(51) Int. Cl.
*A61F 9/00* (2006.01)
*A61L 27/56* (2006.01)
(Continued)

(52) U.S. Cl.
CPC .......... *A61L 27/56* (2013.01); *A61B 17/3417* (2013.01); *A61F 9/0017* (2013.01);
(Continued)

(58) Field of Classification Search
CPC .... A61L 2400/06; A61L 27/50; A61F 9/0017; A61F 9/00781
See application file for complete search history.

(56) References Cited

U.S. PATENT DOCUMENTS

| | | | |
|---|---|---|---|
| 5,520,631 | A | 5/1996 | Nordquist et al. |
| 5,704,907 | A | 1/1998 | Nordquist et al. |

(Continued)

FOREIGN PATENT DOCUMENTS

| | | |
|---|---|---|
| CN | 103037911 A | 4/2013 |
| WO | 03/093196 A1 | 11/2003 |

(Continued)

OTHER PUBLICATIONS

Chen et al., "Wireless Intraocular Pressure Sensing Using Microfabricated Minimally Invasive Flexible-Coiled LC Sensor Implant," *Journal of Microelectromechanical Systems* 19(4):721-734, 2010.

(Continued)

*Primary Examiner* — Kai H Weng
(74) *Attorney, Agent, or Firm* — Seed IP Law Group LLP

(57) ABSTRACT

This disclosure provides a method for reducing or preventing the formation and/or accumulation of drusen in an eye of a mammalian subject in need thereof, the method comprising implanting one or more microporous devices into the eye, each device having a device body and an outer surface, wherein the microporous device is formed of a biocompatible elastomeric material and comprises a plurality of interconnected pores throughout the device body.

17 Claims, 5 Drawing Sheets

(51) Int. Cl.
*A61F 9/007* (2006.01)
*A61B 17/34* (2006.01)
*A61L 27/14* (2006.01)

(52) U.S. Cl.
CPC .......... *A61F 9/00781* (2013.01); *A61L 27/14* (2013.01); *A61L 2400/06* (2013.01); *A61L 2430/16* (2013.01)

(56) References Cited

U.S. PATENT DOCUMENTS

| | | |
|---|---|---|
| 5,807,406 A | 9/1998 | Brauker et al. |
| 5,882,327 A | 3/1999 | Jacob |
| 6,102,045 A | 8/2000 | Nordquist et al. |
| 6,579,235 B1 | 6/2003 | Abita et al. |
| 6,616,699 B2 | 9/2003 | Zilla et al. |
| 6,699,210 B2 | 3/2004 | Williams et al. |
| 6,939,299 B1 | 9/2005 | Petersen et al. |
| 7,037,335 B2 | 5/2006 | Freeman et al. |
| 7,160,264 B2 | 1/2007 | Lisk, Jr. et al. |
| 7,207,965 B2 | 4/2007 | Simon |
| 7,220,238 B2 | 5/2007 | Lynch et al. |
| 7,431,709 B2 | 10/2008 | Pinchuk et al. |
| 7,594,899 B2 | 9/2009 | Pinchuk et al. |
| 7,677,107 B2 | 3/2010 | Nunez et al. |
| 7,678,065 B2 | 3/2010 | Haffner et al. |
| 7,837,644 B2 | 11/2010 | Pinchuk et al. |
| 7,972,628 B2 | 7/2011 | Ratner et al. |
| 8,007,459 B2 | 8/2011 | Haffner et al. |
| 8,152,752 B2 | 4/2012 | Lynch et al. |
| 8,257,295 B2 | 9/2012 | Rickard et al. |
| 8,318,193 B2 | 11/2012 | Ratner et al. |
| 8,372,423 B2 | 2/2013 | Marshall et al. |
| 8,388,568 B2 | 3/2013 | Lynch et al. |
| 8,444,588 B2 | 5/2013 | Yablonski |
| 8,475,374 B2 | 7/2013 | Irazoqui et al. |
| 8,647,393 B2 | 2/2014 | Marshall et al. |
| 8,926,510 B2 | 1/2015 | Marshall et al. |
| 2003/0055372 A1 | 3/2003 | Lynch et al. |
| 2005/0244500 A1 | 11/2005 | Whitcup et al. |
| 2006/0136071 A1 | 6/2006 | Maspero et al. |
| 2006/0276831 A1* | 12/2006 | Porter .................... A61B 17/12 606/200 |
| 2008/0228127 A1 | 9/2008 | Burns et al. |
| 2009/0275924 A1 | 11/2009 | Lattanzio et al. |
| 2009/0299216 A1 | 12/2009 | Chen et al. |
| 2010/0168644 A1 | 7/2010 | Brown |
| 2010/0249691 A1 | 9/2010 | Van Der Mooren et al. |
| 2011/0071456 A1 | 3/2011 | Rickard |
| 2011/0082385 A1 | 4/2011 | Diaz et al. |
| 2011/0098629 A1 | 4/2011 | Juan, Jr. et al. |
| 2011/0196281 A1 | 8/2011 | Lynch et al. |
| 2011/0257623 A1 | 10/2011 | Marshall et al. |
| 2012/0184892 A1 | 7/2012 | Bigler et al. |
| 2012/0220917 A1 | 8/2012 | Silvestrini et al. |
| 2012/0310137 A1 | 12/2012 | Silvestrini |
| 2013/0022648 A1 | 1/2013 | Maginness et al. |
| 2013/0274691 A1* | 10/2013 | de Juan, Jr. ........... A61F 9/0017 604/294 |

FOREIGN PATENT DOCUMENTS

| | | |
|---|---|---|
| WO | 2011/066441 A1 | 6/2011 |
| WO | 2011/127395 A1 | 10/2011 |

OTHER PUBLICATIONS

Kakaday et al., "Design of a Wireless Intraocular Pressure Monitoring System for a Glaucoma Drainage Implant," *Proceedings of the 13th International Conference on Biomedical Engineering*, Singapore, Singapore, Dec. 3-6, 2008, pp. 198-201.

Lim et al., "Glaucoma drainage devices; past, present, and future," *British Journal of Ophthalmology* 82(9):1083-1089, 1998. (8 pages).

Marshall et al., "Quantitative Characterization of Sphere-Templated Porous Biomaterials," *AIChE Journal* 51(4):1221-1232, 2005.

Marshall et al., "Sphere Templated Angiogenic Regeneration (STAR) Biomaterials for Ophthalmic Applications," *Annual Meeting of the Society for Biomaterials*, Seattle, Washington, USA, Apr. 21-24, 2010, 1 page.

Oatts et al., "In Vitro and in Vivo Comparison of Two Suprachoroidal Shunts," *Investigative Ophthalmology & Visual Science* 54(8):5416-5423, 2013.

Patel, "Comparison of Glaucoma Drainage Implants: M4 vs FP7 and S2," *Medscape Ophthalmology*, 2013. (3 pages).

International Search Report and Written Opinion, dated Sep. 27, 2016, for International Application No. PCT/US2016/039389, 13 pages.

Ryan et al., "Retina, Fifth Edition," *Elsevier Saunders* 1:1168-1182, 2012. (16 pages).

* cited by examiner

INJECTABLE POROUS DEVICE FOR TREATMENT OF DRY AND WET AGE-RELATED MACULAR DEGENERATION OR DIABETIC RETINOPATHY

CROSS REFERENCE TO RELATED APPLICATIONS

This application claims the benefit under 35 U.S.C. § 119(e) to U.S. Provisional Application No. 62/184,151, filed Jun. 24, 2015 and U.S. Provisional Application No. 62/204,877, filed Aug. 13, 2015, which applications are hereby incorporated by reference in their entireties.

BACKGROUND

Technical Field

This invention generally relates to age-related macular degeneration (AMD) and diabetic retinopathy, two common diseases of the eye causing progressive vision impairment and blindness.

Description of the Related Art

Age-Related Macular Degeneration (AMD) is a common cause of severe loss of vision in the elderly population. Two subgroups of AMD are distinguished: atrophic (dry form) and exudative (wet form). The dry form (also known as geographic atrophy) is typically characterized by a progressing course leading to degeneration of retinal pigment endothelium and photoreceptors. The exudative form is linked to choroidal neovascularization of the subretinal macular region, with subsequent bleeding and/or fluid leakage, which may result in a sudden loss of vision; it is the most rapidly progressing form of AMD. More than 80% of all people with intermediate and advanced AMD have the dry form, yet this form may progress to the wet form which leads to significantly more vision loss.

The early stage of age-related macular degeneration is associated with minimal visual impairment and is characterized by large drusen and pigmentary abnormalities in the macula. Drusen are accumulations of acellular, amorphous debris subjacent to the basement membrane of the retinal pigment epithelium. Nearly all people over the age of 50 years have at least one small druse in one or both eyes. Only eyes with large drusen are at risk for late age-related macular degeneration.

The presence of drusen is a clinical feature common to both types of AMD. In the "dry" type of macular degeneration, the deterioration of the retina is associated with drusen under the macula, i.e., the formation of small yellow deposits under the macula. This phenomenon is believed to lead to a thinning and drying out of the macula, causing progressive loss of function. The amount of central vision loss is directly related to the location and amount of retinal thinning caused by the drusen.

The dry form of macular degeneration is much more common than the wet type of macular degeneration and it tends to progress more slowly than the wet type. However, a certain percentage of the "dry" type of macular degeneration turns to "wet" with the passage of time. There is no known cure for the "dry" type of macular degeneration.

There are several therapies available for slowing the progression of wet AMD. These are aimed at sealing off leaking blood vessels or preventing re-growth of vessels (anti-angiogenic therapies). All of these require repeated treatments, and none of these can restore vision that has already been lost.

Diabetic retinopathy is a disease of the eye that causes blood vessels to swell and leak fluid around the retina. Treatments available for slowing the progression of diabetic retinopathy include laser sealing of blood vessels and repeated injection of anti-inflammatory drugs.

SUMMARY OF THE INVENTION

Disclosed herein are injectable porous devices capable of preventing the progression of or reversing the pathological symptoms of AMD (both dry and wet forms) and methods for treating AMD by using the same. The devices are also capable of preventing progression of diabetic retinopathy.

More specifically, provided herein is a method for reducing or preventing the formation of drusen in an eye of a mammalian subject in need thereof, the method comprising:

implanting one or more microporous devices into the eye, each microporous device having a device body and an outer surface, wherein the microporous device is formed of a biocompatible elastomeric material and comprises a plurality of interconnected pores throughout the device body and extending to the outer surface, and wherein substantially all the interconnected pores in the microporous device are each interconnected to at least 2 other pores, a mean diameter of the pores being between about 5 and about 50 micrometers, and any two adjacent pores are connected by a throat, a mean throat diameter being at least 5 micrometers.

In particular, the device disclosed herein has a porous biomaterial with pore geometry optimized to attract a high concentration of macrophage cells into its pores when surgically implanted into soft tissue. An especially suitable material is STAR® (Sphere Templated Angiogenic Regeneration) Biomaterial, as described in U.S. Pat. No. 8,318,193, which is incorporated herein by reference in its entirety. Briefly, the suitable biomaterial is formed of an elastomeric material having a plurality of substantially interconnected pores. See also FIG. 2.

The microporous structure of the device makes it possible to attract and build up a sufficient local concentration of functional macrophage cells in proximity to the retina. The scavenging function of these phagocytic macrophage cells can reduce drusen accumulation or reduce the concentration of drusen to nonpathologic level.

The device is capable of increasing the local concentration of macrophage chemotactic factor, which can restore the body's ability to attract functional macrophages for scavenging and removal of drusen and other cellular waste products known to contribute to progression of AMD.

In addition to facilitating the clearance of drusen, the device can prevent the local buildup of inflammatory cytokines that cause the formation of drusen. The pore structure of the device promotes the formation of a permanent "pro-healing" zone in the tissue near the implant. In particular, the immediate surroundings of the porous implant are enriched in favorable M2 phenotype macrophages. M2 macrophages are "pro-healing" because they release anti-inflammatory cytokines that protect tissues from the destructive effects of inflammation. E. M. Sussman et al *Annals of Biomedical Engineering,* 42 (7), 1508-1516 (2014).

Another aspect of the device is that it reduces the local concentration of bacteria in the tissue. This further helps prevent the progression of AMD by alleviating the level of inflammation.

A further aspect of the device is that it is capable of restoring a healthy natural balance of growth factors in the tissue around the device. This can prevent the formation of leaking blood vessels that is characteristic of the more advanced "wet" form of AMD. This aspect of the device also makes it useful for treating diabetic retinopathy.

In some embodiments, the device may comprise a single device, while in other embodiments, it may comprise a plurality of porous granules, rods, or other shapes, as described in U.S. Pat. No. 8,927,022, which is incorporated herein by reference in its entirety.

In some embodiments, the device can be implanted into the subcleral space, retrobulbar space, peribulbar space, sub-tenon's space, vitreous humour, or other tissue of the eye by injecting through a needle or other tubular insertion device. An elongated rod shape is particularly well-suited for this.

In some embodiments, the device may be inserted via an ab interno approach (inserting a needle through the cornea to reach the desired tissue).

Another aspect of the present invention is that the preferred embodiments are both compressible (due to porosity) and elastic (due to elastomeric material). It is possible to squeeze the device into a tubular needle with smaller internal diameter than the diameter of the device. It also allows for the device to exit the needle during implantation.

In some embodiments, multiple injections may be used in combination in order to achieve efficacy.

In some embodiments, the device may be larger than an injectable size, in which case it can be surgically placed through an incision into a subscleral pocket or other tissue of the eye.

In some embodiments, the device may be preloaded with drugs or other biologically active agents, such as anti-inflammatories, antibiotics, or biologically active proteins. In some embodiments, the loaded drug may be released over time. In other embodiments, the drug may provide activity while permanently linked to the device. An advantageous aspect of the invention is that the pore geometry is resistant to infection. The surfaces of the pores within the device become fully covered with adherent macrophages of anti-bacterial phenotype. In this way, the device harnesses the body's natural defense mechanisms to provide lasting anti-bacterial activity.

DETAILED DESCRIPTION

To date, there is no effective treatment available for dry AMD. A primary contributor to the progression of AMD is the formation and accumulation of drusen.

Disclosed herein are implantable devices capable of preventing formation and accumulation of drusen. Extracellular deposits known as "drusen" have been known to accumulate within the eyes of human beings as they age. Drusen can be observed directly under funduscopic examination and may be classified as either soft drusen or hard drusen, depending on relative size, abundance, and shape. Drusen typically forms beneath the basement membrane of the retinal pigmented epithelium (RPE) and the inner collagenous layer of Bruch membrane. Excessive or confluent areas of drusen in the macula are associated with the development of chorioretinal disorders, such as age-related macular degeneration (AMD). The devices are thus capable of preventing the progression of AMD and/or reducing the pathological symptoms of the disease.

The device is capable of providing benefits for both "dry" AMD and "wet" AMD patients. The device or implant is microporous and is designed to be injected into the tissue of the eye, such as into the retrobulbar space or peribulbar space behind the retina. Alternative embodiments of the device can be injected into the subscleral space or into the vitreous humour.

Provided herein is a method for reducing or preventing the formation of drusen in an eye of a mammalian subject in need thereof, the method comprising implanting one or more microporous devices into the eye, each microporous device having a device body and an outer surface, wherein the microporous device is formed of a biocompatible elastomeric material and comprises a plurality of interconnected pores throughout the device body and extending to the outer surface.

Thus, the microporous device has an open-cell structure, which comprises interconnected pores throughout the entire bulk of the device body and extending to the device surface.

Figure 1A:
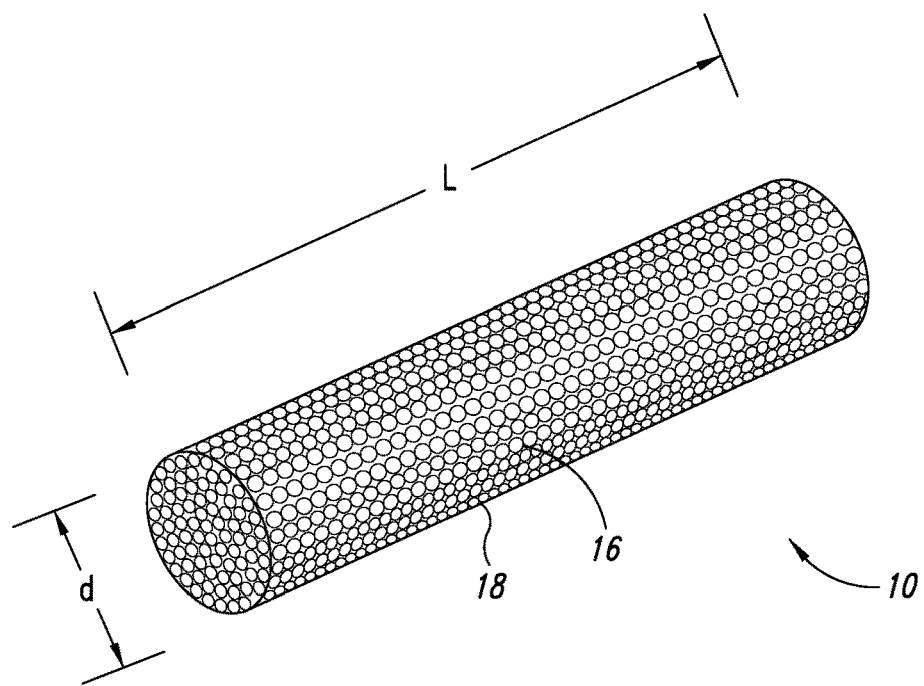
FIG. 1A is a schematic drawing of an injectable soft porous rod-shaped device according to one embodiment of the present disclosure.

FIG. 1A is a schematic drawing of an embodiment of the present disclosure that shows the device body 10 having an elongated rod shape with length (L) and diameter (d). The device body is of a soft porous material having pores (16) within the device body and extends to the outer surface (18). In various embodiments, the length is within the range of 3-10 mm, or more typically, within the range of 3-5 mm. In various embodiments, the diameter is within the range of 0.2-0.8 mm, or more typically, within the range of 0.4-0.6 mm.

While rod shapes are particularly compatible with injection, the device or implant of the present disclosure can be in any shapes and be inserted by any means known to a skilled person in the art. In some embodiments, a flat sheet shape may be useful to allow enough device volume and surface area for sufficient efficacy. Generally speaking, the longest dimension of the device, regardless of the shape, is about 3-10 mm; whereas the thickness of the device (e.g., the diameter of a rod shape device, or the thickness of a sheet-shaped device) is about 0.2-0.8 mm.

Figure 1B:
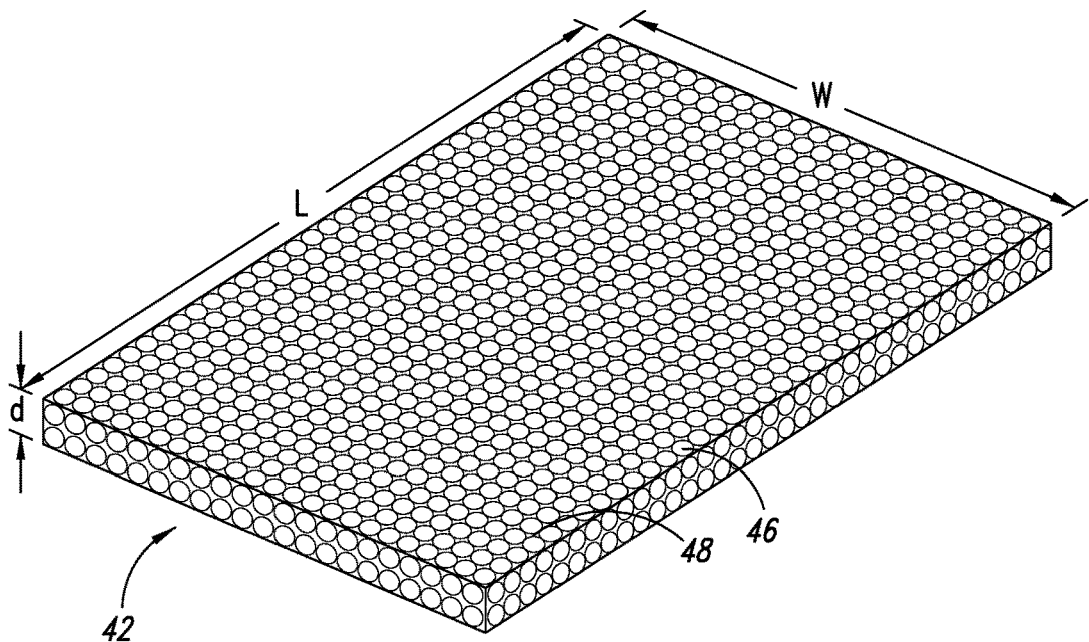
FIG. 1B is a schematic drawing of a soft porous sheet-shaped device according to one embodiment of the present disclosure.

FIG. 1B is a schematic drawing of another embodiment of the device body 42 which is a sheet or film of the microporous material. As in the rod-shaped device, the sheet has pores (46) throughout its entire device body and extending to the outer surface (48). The length (L), width (W) and thickness (d) are not particularly limited other than that the sheet fits in an anatomical space or surgically-created space in the eye. The sheet thickness should be thin enough to fit into the desired tissue space. For example, a thickness (d) is about 0.2 mm to 0.8 mm, or preferably about 0.2 mm-0.5 mm.

Figure 2:
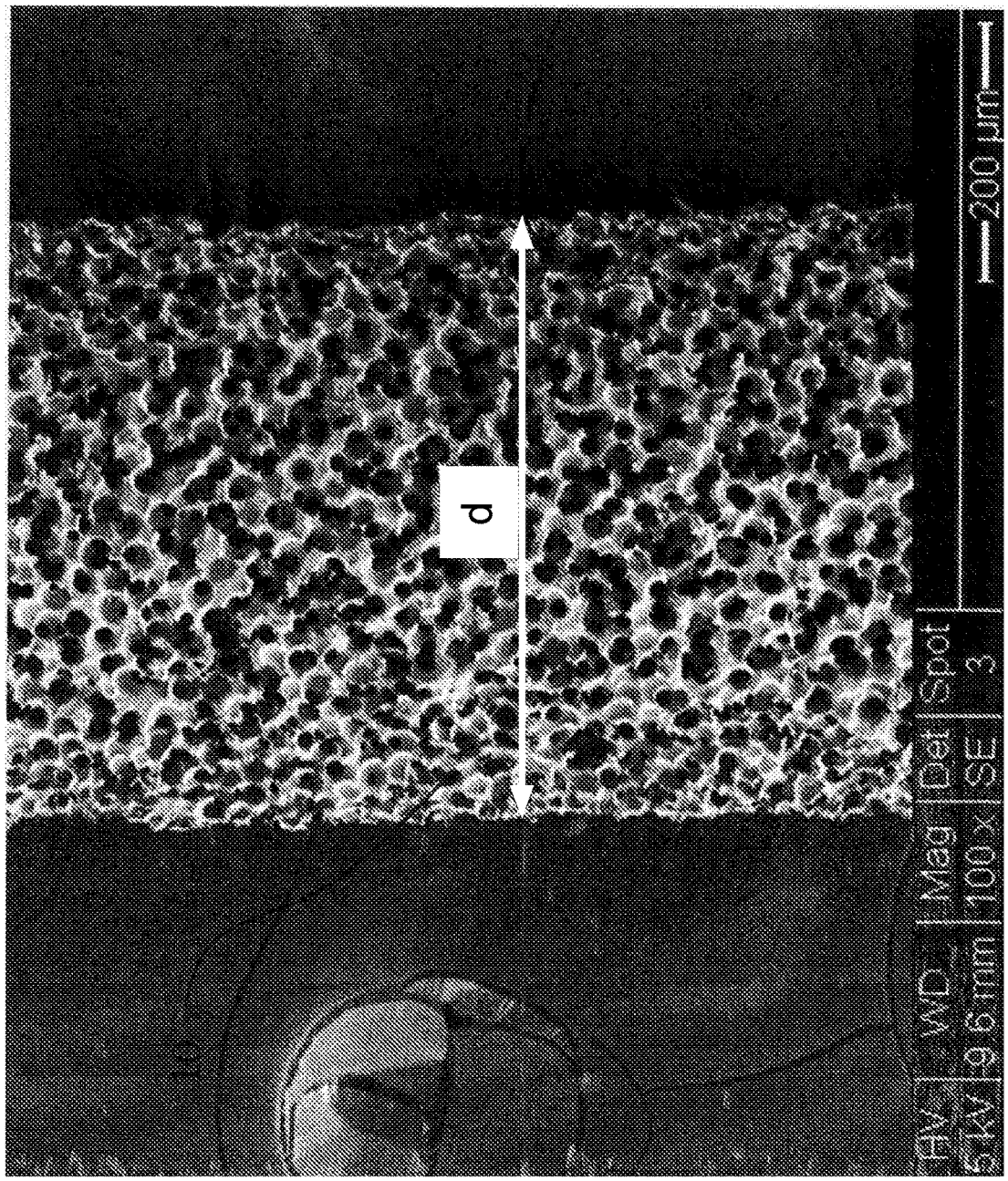
FIG. 2 is a scanning electron microscopy (SEM) image of an injectable soft porous rod-shaped device of according to one embodiment.

FIG. 2 is a scanning electron microscopy (SEM) image showing a rod-shaped device body 10 according to one embodiment of the present disclosure. The device body is made of a biocompatible material, e.g., an elastomeric material, and comprises a plurality of substantially interconnected pores. In preferred embodiments, the device is composed of a sphere-templated silicone material as described in U.S. Pat. No. 8,318,193.

Figure 3:
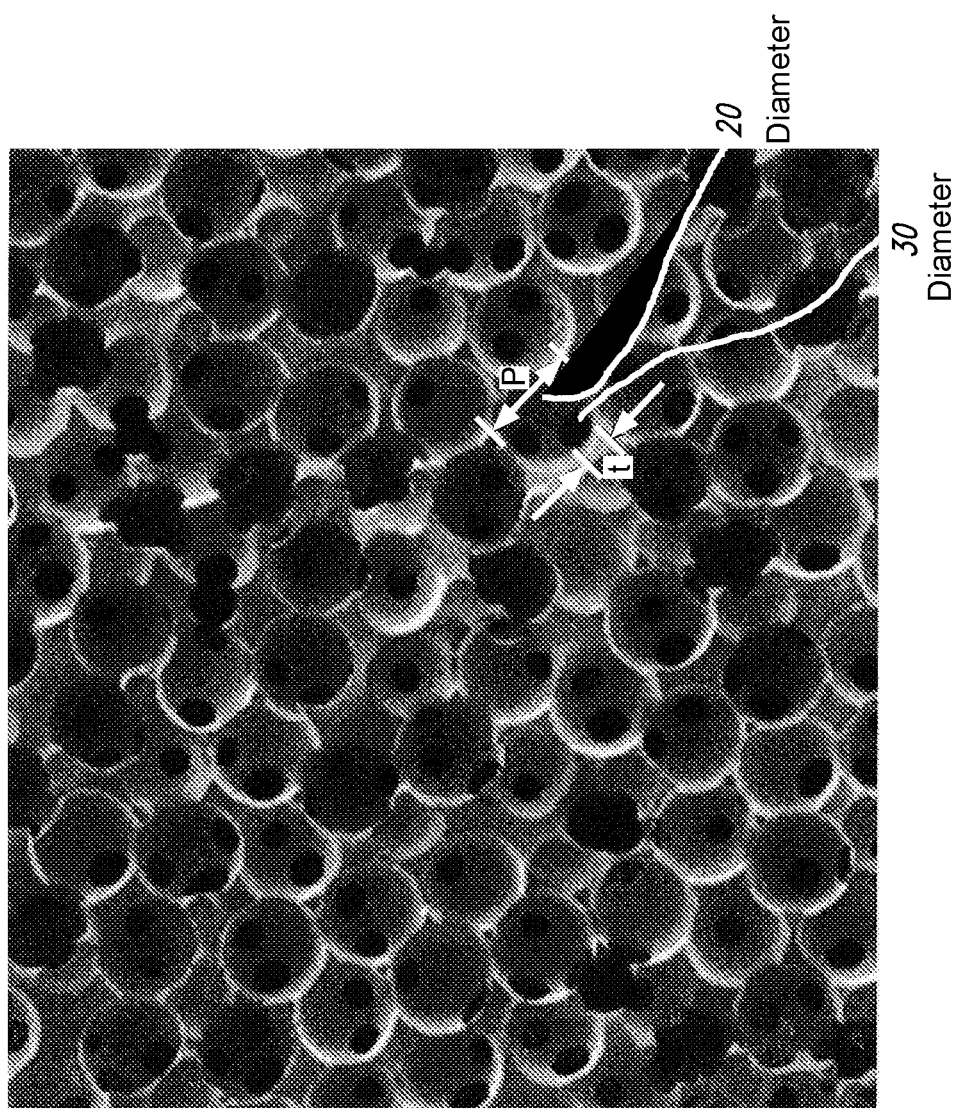
FIG. 3 shows the open-pore structure of the device, indicating pore and throat dimensions.

FIG. 3 is a scanning electron microscopy (SEM) image showing the cross section of a device of the sphere-templated porous biomaterial that is particularly suitable for the present invention. The pore structure comprises a network of interconnected void spaces referred to herein as pores 20. Neighboring pores 20 are joined or connected by openings or "throats" 30. The pores 20 can be spherical as in FIG. 2, or they can be any other pore shape that results in a generally open-cell pore structure. The throats 30 can be circular as in FIG. 2, or they can be any other 2D shape that defines the size of the openings between neighboring pores 20. If the pore throats are not circular, then the throat diameter t is defined as the diameter of the largest spherical object that can pass through the throats 30.

Advantageously, the pore sizes and the throat diameters (i.e., dimensions of the openings between adjoining pores) can be controlled to allow macrophages or neutrophils to infiltrate, as well as enhance the accessible areas for the macrophages and neutrophils. Thus, in certain embodiments, substantially all the interconnected pores (i.e., at least 90%, or at least 95% or at least 98%) in the microporous device are each interconnected to at least 2 other pores, a mean diameter of the pores being between about 5 and about 50 micrometers, and any two adjacent pores are connected by a throat, a mean throat diameter being at least 5 micrometers, or at least 8 microns, or at least 10 microns. In preferred embodiments, the mean throat diameter is between about 8 to about 15 microns. As used herein, "substantially all of the pores" means at least 90%, or at least 95% or at least 98% of all of the pores. In addition, "about" refers to a range of values ±20% of a specified value. For example, the phrase "about 10 micrometers" includes a range of ±20% of 10 micrometers, namely, 8-12 micrometers.

In accordance with the present disclosure, throat diameter t is large enough to permit host macrophages and neutrophils to infiltrate the pore structure. These cells are capable of attacking and destroying bacteria and preventing bacterial colonization. A human macrophage is typically 15-20 microns in diameter, but is capable of squeezing through openings as small as 5 microns in diameter. A neutrophil is similar in size to a macrophage. Accordingly, the throat diameter t should be at least 5 microns. In various embodiments, the throat diameter should be at least 8 microns, or at least 10 microns.

To the extent that throat diameters smaller than 5 microns may be formed in the course of producing the porous material (e.g., according to the methods disclosed in U.S. Pat. No. 8,318,193), care should be taken to minimize the percentage of these smaller throat diameters. A bacterial cell is much smaller than a macrophage, typically 1 to 2 microns in size. Pores having throats in the 1 to 5 micron size range can allow bacteria to enter while preventing access to the much larger macrophages and neutrophils that would ordinarily attack and destroy the bacteria. Thus, in certain embodiment, only a very small percentage of throats (less than 2%, more preferably less than 1%) have diameter t in the 1 to 5 micron size range.

In other embodiments, at least 90% of all the throats in the microporous device have diameters of at least 5 microns. In various other embodiments, at least 95%, or at least 98% or at least 99% of all the throats in the microporous device have diameters of at least 5 microns.

In other embodiments, at least 90% of all the throats in the microporous device have diameters of at least 5 microns. In various other embodiments, at least 95%, or at least 98% or at least 99% of all the throats in the microporous device have diameters of at least 5 microns.

In other embodiments, at least 90% of all the throats in the microporous device have diameters of at least 8 microns. In various other embodiments, at least 95%, or at least 98% or at least 99% of all the throats in the microporous device have diameters of at least 8 microns.

A further important feature is that the pore structure has high bioavailable surface area, where "bioavailable surface area" is defined as the surface area accessible to macrophages. Surface area is inversely proportional to pore size, so the size of the pores 20 is an important parameter for measuring the bioavailable surface area. The average or mean pore diameter P should be less than 50 microns, more preferably less than 40 microns, and most preferably less than 30 microns. It is preferable that the pore size be the smallest possible size wherein the pores can be interconnected by throats of the optimal 8 to 15 micron size range. Preferably, the throat diameter t should be about 40% of the pore diameter P, such as between 30% and 45%, or between 35% and 45%. Throat-size-to-pore-size ratios too large render the pore structure mechanically fragile, so ratios larger than 45% are undesirable. Conversely, ratios smaller than 30% may have larger pores and thus lower bioavailable surfaces area, so that the device does not attract macrophages into its porous interior at effective concentrations for antibacterial defense or therapeutic efficacy.

Smaller devices are less invasive to insert and more than one may be implanted to different locations of the eye. In various embodiments, the total outer surface areas of the device or implant (regardless of the shapes or numbers of the implants) may be in the range of 3-250 $mm^2$, or 25-200 $mm^2$.

The device can be made from any elastomeric polymer. A particularly suitable polymer is silicone rubber. Nusil MED-4830, MED-4840, MED-4850, MED-4860, and MED-6215 are particular suitable compositions. Other possible biostable materials include polyurethanes, polypropylene, polyethylene, cellulose nitrate, cellulose acetate, polytetrafluoroethylene, or hydrogels. In some embodiments, the device can be made from a biodegradable polymer.

In some embodiments, the device may be made from a transparent biomaterial having a refractive index very close to that of the vitreous humour. This is advantageous for embodiments where the device is injected into the vitreous humour, as the close match in refractive index between the porous biomaterial and the ingrown vitreous humour inside the pores ensures translucency to minimize interference with the light path to the retina. An exemplary transparent biomaterial is NuSil MED-6250 silicone elastomer, which has refractive index of 1.41. The refractive index of vitreous humour is 1.37.

Most preferably, the elastomeric polymer should have a low durometer value when measured in its nonporous form, ideally between 30 and 60 Shore A. A low durometer value combined with porosity is less irritating and less inflammatory to tissues than more rigid materials. And preferably, the elastomeric polymer should have maximum elongation strain greater than 100%, more preferably greater than 300%, and most preferably greater than 500%. In some embodiments, high elongation facilitates injection through a needle or insertion tool.

It is desirable for an injection needle or insertion tool to have a small diameter (typically 0.2-0.3 mm ID) so that trauma to the eye tissues is minimized during the insertion procedure. For the device to be large enough to provide effective therapeutic strength and strong enough to resist damage during loading into the bore of the insertion needle, a diameter of at least 0.5 mm is preferable. The inner diameter of the tubular needle or insertion tool is preferably substantially smaller in diameter than the outer diameter of the device. Thus, it would be advantageous for the device to be compressed to less than half of its relaxed diameter before loading it into the insertion tool. One way to accomplish such radial compression is to stretch the device under axial tension to at least 300% strain. Silicones and other similar elastomeric materials have a Poisson's ratio of nearly 0.5, so for example, a 300% axial tensile strain produces a radial compression to a compressed diameter of about 50% of the relaxed diameter.

Figure 4:
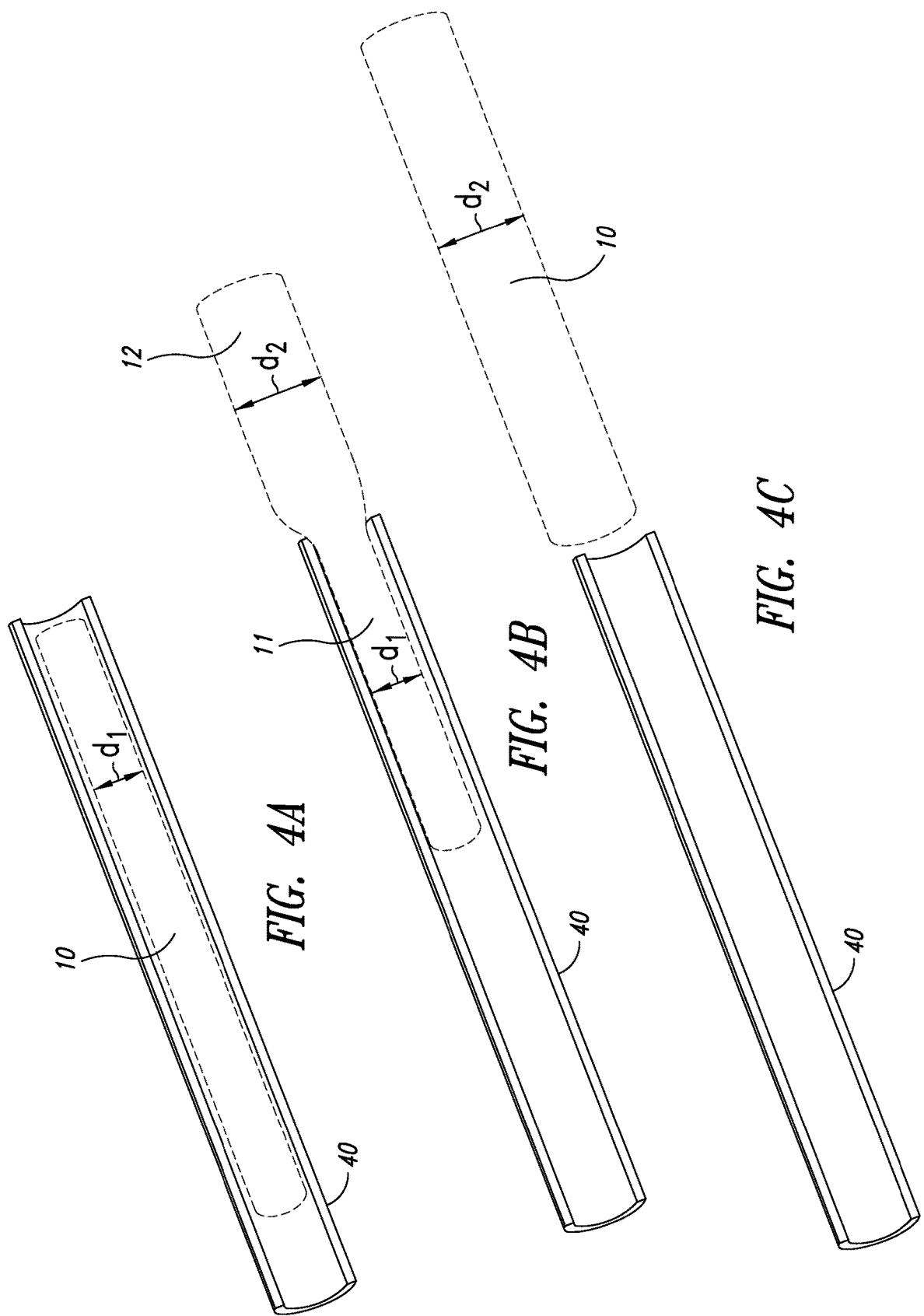
FIGS. 4A-4C show schematically a soft porous injectable rod-shaped device being radially compressed within the bore of an injection needle (FIG. 4A), partially ejected from the end of the needle (FIG. 4B), and fully ejected beyond the tip of the needle (FIG. 4C).

FIG. 4A shows a cross-sectional drawing of an injection needle 40 with radially compressed soft porous device body 10 fully inside the bore of the needle having an internal diameter $d_1$. The compressed device has a compressed diameter that is the same as the internal diameter $d_1$. FIG. 4B shows the radially compressed proximal end 11 of the device body 10 inside the end the needle and the partially ejected radially expanded distal end 12 of the device body 10 beyond the distal tip of the needle. The portion of the device that is outside of the needle expands into its relaxed diameter $d_2$. FIG. 4C shows the device body 10 fully expanded and fully ejected beyond the distal end of the injection needle.

A further embodiment provides a needle preloaded with a microporous device comprising: a needle having an interior diameter of 0.2-0.3 mm, a microporous device having a relaxed diameter of 0.3-0.8 mm, wherein the microporous device is radially compressed and placed in the needle such that the needle and the microporous device are aligned longitudinally, and wherein the microporous device is as described herein.

A "relaxed diameter" is the diameter of the microporous device in its natural, uncompressed shape, which may be the shape prior to being inserted into the needle, the shape after exiting the needle, or the shape while being implanted in the eye.

To radially compress the microporous device, the device may be axially stretched. There are a number of ways to load an axially stretched device into the bore of the needle or insertion tool. One method comprises the steps of: 1) hydrating the pores of the device in aqueous biocompatible saline solution or other biocompatible aqueous substance, 2) elongating the device by gripping the ends and applying an axial strain, 3) flash freeze the aqueous solution within the pores of the hydrated and stretched device (e.g., by submerging in liquid nitrogen or other low-boiling point liquid), 4) loading the narrowed and elongated device (stiffened by the frozen water within the pores) into the tubular nose member of the insertion tool, and 5) allowing the aqueous solution to thaw, causing the device to expand against the inner wall of the tubular needle. Once loaded in this way, the device is ready for injection into the retrobulbar space (or other suitable site in close proximity to the retina) by application of gentle fluid pressure.

Figure 5:
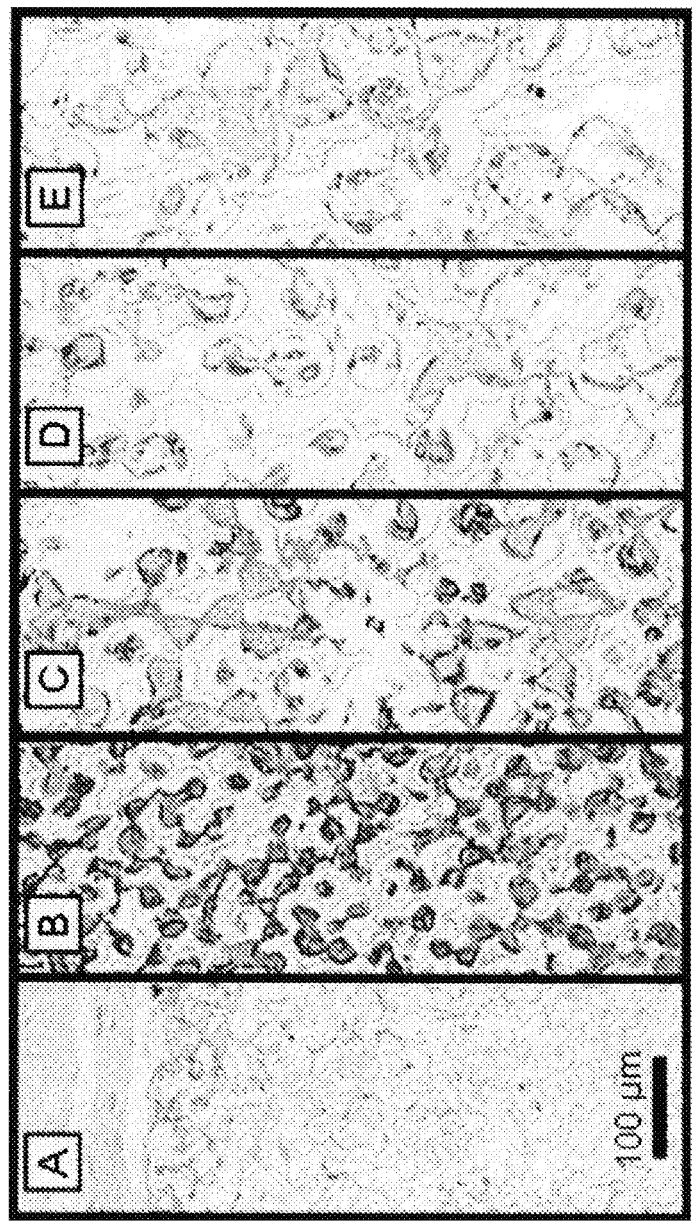
FIG. 5 shows tissue sections of sphere-templated microporous scaffolds of various pore diameters implanted subcutaneously in mice for 28 days; sections have been stained with BM8 macrophage marker. Pore sizes: (A) 20 micrometers; (B) 35 micrometers; (C) 50 micrometers; (D) 70 micrometers (E) 90 micrometers. The scaffold with 35-micrometer pores contains the highest concentration of macrophages.

FIG. 5 shows a correlation between the pore sizes and the local concentrations of macrophages. See also Marshall A J. Porous hydrogels with well-defined pore structure for biomaterials applications. Ph.D. Dissertation, University of Washington. 2004 AAT 3151637.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

The invention claimed is:

1. A method for treating or preventing age-related macular degeneration from progressing in an eye of a mammalian subject in need thereof, the method comprising:
    inserting one or more microporous devices through an insertion tool into the eye, each microporous device having a device body and an outer surface, wherein the microporous device is contained within the insertion tool in a compressed state prior to inserting; and wherein the microporous device expands from the compressed state after exiting from the insertion tool to effect implantation of the one or more microporous devices, thereby reducing the formation or accumulation of drusen in the eye;
    wherein each microporous device is formed of a biocompatible elastomeric material and comprises a plurality of interconnected pores throughout the device body and extending to the outer surface, and
    wherein substantially all the interconnected pores in the microporous device are each interconnected to at least 2 other pores, a mean diameter of the pores being between about 5 and about 50 micrometers, and any two adjacent pores are connected by a throat, a mean throat diameter being at least 5 micrometers.

2. The method of claim 1 wherein the mammalian subject suffers from atrophic or exudative age-related macular degeneration.

3. The method of claim 1 wherein the mean throat diameter is at least 8 microns.

4. The method of claim 1 wherein the mean throat diameter is about 8 to 15 microns.

5. The method of claim 1 wherein less than 2% of the interconnected pores have a mean throat diameter in the range of 1 to 5 microns.

6. The method of claim 1 wherein less than 1% of the interconnected pores have mean throat diameter in the range of 1 to 5 microns.

7. The method of claim 1 wherein at least 90% of all the throats in the microporous device have diameters of at least 5 microns.

8. The method of claim 1 wherein at least 95% of all the throats in the microporous device have diameters of at least 5 microns.

9. The method of claim 1 wherein at least 90% of all the throats in the microporous device have diameters of at least 8 microns.

10. The method of claim 1 wherein at least 90% of all the throats in the microporous device have diameters of about 8-15 microns.

11. The method of claim 1 wherein the interconnected pores have a mean pore diameter of less than 50 microns.

12. The method of claim 11 wherein the mean pore diameter is less than 40 microns.

13. The method of claim 11 wherein the mean pore diameter is less than 30 microns.

14. The method of claim 1 where the microporous device is about 3-10 mm long.

15. The method of claim 1 where the microporous device is about 0.2-0.8 mm thick.

16. The method of claim 1 wherein the microporous device is of a rod shape or a sheet shape.

17. The method of claim 1 wherein the biocompatible elastomeric material is silicone rubber, polyurethanes, polypropylene, polyethylene, cellulose nitrate, cellulose acetate, polytetrafluoroethylene, hydrogel, or a combination thereof.

\* \* \* \* \*